(12) United States Patent
Hartl

(10) Patent No.: US 11,598,386 B2
(45) Date of Patent: Mar. 7, 2023

(54) SPRING MECHANISM AND HYDRAULIC ACTUATOR

(71) Applicant: Otto Bock Healthcare Products GmbH, Vienna (AT)

(72) Inventor: Stefan Hartl, Vienna (AT)

(73) Assignee: Otto Bock Healthcare Products GmbH, Vienna (AT)

( * ) Notice: Subject to any disclaimer, the term of this patent is extended or adjusted under 35 U.S.C. 154(b) by 272 days.

(21) Appl. No.: 15/733,066

(22) PCT Filed: Sep. 17, 2018

(86) PCT No.: PCT/EP2018/075085
§ 371 (c)(1),
(2) Date: May 6, 2020

(87) PCT Pub. No.: WO2019/091642
PCT Pub. Date: May 16, 2019

(65) Prior Publication Data
US 2021/0102593 A1    Apr. 8, 2021

(30) Foreign Application Priority Data
Nov. 10, 2017    (DE) .................. 10 2017 126 396.9

(51) Int. Cl.
| F16F 3/02 | (2006.01) |
| A61F 2/64 | (2006.01) |
| A61F 2/66 | (2006.01) |
| A61F 2/68 | (2006.01) |
| A61F 5/01 | (2006.01) |
| F16F 13/00 | (2006.01) |
| A61F 2/74 | (2006.01) |

(52) U.S. Cl.
CPC ................. *F16F 3/02* (2013.01); *A61F 2/64* (2013.01); *A61F 2/66* (2013.01); *A61F 2/68* (2013.01); *A61F 5/0123* (2013.01); *F16F 13/005* (2013.01); *A61F 2/74* (2021.08); *A61F 2002/6614* (2013.01); *A61F 2005/0179* (2013.01)

(58) Field of Classification Search
CPC combination set(s) only.
See application file for complete search history.

(56) References Cited

U.S. PATENT DOCUMENTS

| 4,714,148 A | 12/1987 | Alas et al. |
| 5,888,212 A * | 3/1999 | Petrofsky .................. F16F 9/46 |
| | | 623/44 |
| 5,906,361 A | 5/1999 | Carranza |
| 8,834,539 B2 * | 9/2014 | Keren ...................... F16B 43/00 |
| | | 606/305 |
| 2005/0038515 A1 * | 2/2005 | Kunzler ................ A61F 2/4425 |
| | | 623/17.13 |

(Continued)

FOREIGN PATENT DOCUMENTS

| CN | 2151336 Y | 12/1993 |
| DE | 1024769 A | 8/1958 |

(Continued)

*Primary Examiner* — Monica E Millner
(74) *Attorney, Agent, or Firm* — Holland & Hart LLP

(57) ABSTRACT

A spring mechanism having at least two wave washers and at least one spring washer between the wave washers. The wave washers are mounted so as to be twistable relative to one another.

20 Claims, 11 Drawing Sheets

(56) References Cited

U.S. PATENT DOCUMENTS

| | | |
|---|---|---|
| 2006/0066016 A1 | 3/2006 | Hasegawa et al. |
| 2009/0192617 A1* | 7/2009 | Arramon ............... A61F 2/4425 623/17.13 |
| 2009/0192625 A1 | 7/2009 | Boiten |
| 2011/0213425 A1 | 9/2011 | Keren et al. |
| 2012/0136356 A1* | 5/2012 | Doherty ............... A61B 17/725 606/62 |
| 2013/0085580 A1* | 4/2013 | Wu ......................... A61F 2/644 623/43 |
| 2013/0139502 A1 | 6/2013 | Chu |
| 2016/0009523 A1* | 1/2016 | Omarsson ............ A43C 11/165 242/395 |

FOREIGN PATENT DOCUMENTS

| | | | |
|---|---|---|---|
| DE | 102006009510 A1 | 9/2007 | |
| DE | 102012108322 A1 | 6/2013 | |
| EP | 549855 A2 * | 7/1993 | .............. A61F 2/64 |
| FR | 1112231 A | 3/1956 | |
| JP | 2001116010 A | 4/2001 | |
| WO | 2009077099 A1 | 6/2009 | |
| WO | 2011001132 A2 | 1/2011 | |
| WO | 2014198529 A1 | 12/2014 | |
| WO | 2015101417 A1 | 7/2015 | |

* cited by examiner

SPRING MECHANISM AND HYDRAULIC ACTUATOR

CROSS REFERENCE TO RELATED APPLICATIONS

This application is a U.S. National Entry and claims priority to PCT International Patent Application No. PCT/EP2018/075085, filed 17 Sep. 2018, and entitled "SPRING MECHANISM AND HYDRAULIC ACTUATOR," which claims priority to Germany Patent Application No. 10 2017 126 396.9 filed 10 Nov. 2017, the entire disclosures of which are incorporated herein by this reference.

TECHNICAL FIELD

The invention relates to a spring device having at least two wave washers and at least one spring washer disposed between the wave washers, as well as to a hydraulic actuator having such a spring device.

BACKGROUND

Energy accumulators for storing mechanical energy can be configured in various ways. Apart from hydraulic and pneumatic energy accumulators, there are mechanical energy accumulators in which energy is stored by way of an elastic deformation. A reverse deformation takes place in order for said energy to be released, this thus being an elastic deformation or a reversible deformation. Mechanical springs which can be constructed in various ways are such energy accumulators. Apart from elastomer elements, plastics-material springs, springs from fiber-reinforced plastics materials, or metal springs can be used for mechanically accumulating energy. Common construction modes of such springs are leaf springs, spiral springs, or else helical or coil springs.

The spring preload, in particular in the case of coil springs, can be set by modifying the initial spring length.

In particular in the case of orthopedic devices such as orthotics or prosthetics having a system for recovering energy during a movement, there is the problem that only limited installation space is available, and a storage spring in terms of the quantity of energy to be received, or the quantity of energy to be released, respectively, in energy recovery systems may be difficult to adapt to the respective operating states and requirements. Therefore, non-adjustable storage springs which have to be selected so as to be adapted to the respective specific use and the respective patient are often used.

SUMMARY

It is therefore an object of the present invention to provide a spring device and a hydraulic actuator having such a spring device, which requires a small installation space and is adjustable to the respective specific use. Potential dissimilar specific uses include, in particular, the individualization in terms of the patient as well as the adaptation to changing operating states of machines such that the required or desired adaptations can be performed in the field of control technology.

This object is achieved according to the invention by a spring device having the features disclosed herein, and by a hydraulic actuator. Advantageous embodiments and refinements of the invention are also disclosed herein with reference to the description and figures.

The spring device according to the invention having at least two wave washers provides that at least one spring washer is disposed between two wave washers, wherein the wave washers are mounted so as to be capable of being rotated relative to one another. A stepless adaptation to the respective specific use can take place on account of the rotatable disposal of the two wave washers between which the at least one spring washer is disposed. The stroke of the spring device can be set by the rotation of the one wave washer relative to the other wave washer. When the respective maxima and elevations of the mutually opposite wave washers are situated in a position in which said maxima and elevations are directly opposite one another, the spring washer is situated directly between the two maxima, whereby no axial relative movement of the two wave washers toward one another is however possible. Accordingly, the spring washer which is preferably configured as a flat, in particular metallic, spring washer cannot be elastically deformed. Rather, only a negligible compression of material takes place in the region of the mutually opposite maxima. The effective spring deflection of the spring unit is thus equal to zero. When the two spring washers are rotated relative to one another such that a maximum is opposite a minimum, thus an elevation is opposite a depression, maximum repositioning in the axial direction, thus in the direction of the wave washers toward one another, is possible. On account thereof, a maximum deformation of the spring washer or spring washers that is/are disposed between said wave washers is possible, on account of which a maximum quantity of energy can be stored. A stepless adjustment of the spring device between those limit settings in terms of stiffness and preload by way of a mechanical spring device is provided on account of the mutual rotatability of the two wave washers. Only a small installation volume, in particular in an axial extent, is required, and no additional compensation volume is moreover required when said spring device is used in a hydraulic system, in particular in a hydraulic actuator such as a hydraulic damper or a hydraulic activation device.

A refinement of the invention provides that a plurality of spring washers as a spring washer stack are disposed between two wave washers. A simple adaptation to the desired spring stiffness or to the desired quantity of energy to be stored and released can be achieved by adding or removing a spring washer on account of disposing a plurality of spring washers in series and combining a plurality of spring washers so as to form a spring washer stack. For example, an adaptation to patients who use an orthopedic system with a hydraulic actuator, to different levels of activity, or to different weight classes, can take place on account thereof.

In a refinement of the invention it is provided that a wave washer which is disposed on the end of that side that faces away from the spring washer is configured so as to be flat. Wave washers can thus preferably have a wave shape which in a lateral view have a sinusoidal profile on the upper side and on the lower side. In order for an ideally small installation volume to be able to be implemented and for the spring pressure to be able to be uniformly discharged to a counter bearing, only that surface of a wave washer disposed at the end side that is assigned to the spring washer is configured so as to be undulated. The rear side is configured so as to be flat such that a fully planar and not only linear bearing is present in those regions of the elevations that are configured as depressions on the opposite side. In the case of only two wave washers and one spring washer disposed therebetween, or one spring washer stack disposed therebetween, both wave washers are configured so as to be flat on sides that faces away from one another.

In an embodiment having more than two wave washers it is preferably provided that a wave washer which is configured so as to be undulated on both sides that face the spring washers is disposed between two spring washers or two spring washer stacks. By disposing a plurality of wave washers in series, having spring washers disposed therebetween, it is possible for the maximum stroke as well as the maximum quantity of energy to be stored to be set. The more wave washers disposed behind one another, the larger the maximum stroke and the maximum quantity of energy to be stored. The wave washers disposed between two wave washers disposed at the end side are preferably configured so as to be undulated such that the respective maxima lie in one plane. The planes in which the respective maxima are situated are preferably configured so as to be mutually parallel, which means that the maxima on the front side and the maxima on the rear side of a wave washer are in each case in one plane, wherein said planes are preferably oriented so as to be mutually parallel. When all maxima or elevations of the wave washers are mutually aligned such that the maxima of neighboring wave washers are directly opposite one another, the maximum length of the spring device is achieved but a spring effect can nevertheless not be achieved since no mutual relative repositioning of the wave washers can take place in the axial direction. When the wave washers are mutually aligned such that the maxima and minima of neighboring wave washers are mutually aligned, a maximum repositioning in the axial direction can take place, and a maximum quantity of energy can thus be stored and released.

The wave washers can be produced by primary shaping, subtractive machining of a flat spring washer, or by forming. The wave washers are preferably produced from a solid, in particular rigid, material, for example steel or any other dimensionally stable metal, or from a fiber-reinforced plastics material, for example.

The wave washers and the at least one spring washer, or all spring washers, in one variant have in each case a central clearance and in a refinement of the invention are mounted on a central guide. The spring washer or spring washers, as well as the wave washers are thus configured as annular washers. On account of the disposal on a central guide, it is possible for an axial repositioning of the wave washers toward one another or away from one another to be guided such that a linear movement can be reliably carried out without any lateral deflection movement being able to take place. The central clearance is preferably round, or at least permits mutual rotation of the wave washers. Along with it, the central clearances can be configured so as to deviate from a round design embodiment, for example having a form-fit element or a flattening or a protrusion, so as to guarantee an anti-rotation safeguard of the wave washers, or at least one wave washer, relative to the central guide when this is required or desired.

At least one wave washer can be coupled to an adjustment device by way of a form-fit element so as to enable mutual rotation of the wave washers. The form-fit element can be configured as a protrusion or a clearance, in particular as a safety pin or a bore for receiving a pin or an engagement element; it is likewise possible that an internal contour or an external contour which is configured so as not to be rotationally symmetrical functions as a form-fit element. For example, the external contour of the wave washer can have a flattening or a polygonal shape, wherein the adjustment device has a corresponding flattening, contour, or a corresponding protrusion such that the wave washer is entrained in a rotation of the adjustment device about a rotation axis, and said wave washer is moved about the rotation axis relative to a second wave washer which is mounted in a rotationally fixed manner or is rotated in another direction. In the case of a mounting about a central guide, the form-fit element, or the form-fitting coupling of the adjustment device to the wave washer, can be by way of the central clearance, for example by way of an unround design embodiment of the central guide by way of a corresponding shaping of the central clearance. In the case of a disposal of the wave washers at the end side or the front side, it is possible by way of a form-fitting connection which engages on the end face that faces away from the respective spring washer, in particular the outer end face of the wave washer, such that rotation relative to the respective other wave washer is possible. The form-fit element, or the form-fit elements, can be configured as a clearance, a protrusion, a pin, a shoulder, an unroundness, or a toothing. There is in principle the possibility that, in the case of an undulated shaping of the wave washer on both sides, a form-fitting coupling of the wave washer and the adjustment device takes place by way of a corresponding undulation of the adjustment device. As an alternative to an establishment by way of a form-fit element, or a plurality of form-fit elements, at least one wave washer can be coupled in a force-fitting or materially integral manner, for example by being clamped or adhesively bonded to the adjustment device. An adjustment by way of a force-transmission element is also possible and provided.

The adjustment device can at least partially surround the wave washer, or be at least partially disposed within the adjustment device. For example, the adjustment device can have a sleeve which is disposed outside the wave washer and surrounds the latter such that, apart from rotation, guiding in the axial direction is simultaneously provided by the adjustment device. Alternatively or additionally to an external adjustment device circumferentially disposed on the wave washer, said adjustment device can also be disposed within the wave washer in the respective clearance so as to there enable rotation about a longitudinal axis or rotation axis. There is also the possibility for a plurality of adjustment devices to be present, for example an external adjustment device which surrounds the wave washer, and an internal adjustment device which is disposed in a central clearance, said two adjustment devices potentially acting in an opposing manner such that two wave washers are mutually rotated in that both wave washers are rotated in opposite directions.

The adjustment device is advantageously driven in a motorized manner, in particular by an electric motor, so as to be able to perform in orthopedic devices, for example orthotics or prosthetics, during use an adaptation of the spring deflection, the stiffness, and the quantity of energy to be received or released. The motor is capable of being driven in one or another direction by way of a control device such that an increase as well as a decrease of the spring deflection length and of the energy to be received can advantageously be performed with only one motor. A plurality of adjustment devices can also be driven by one motor, and a contra rotating adjustment movement of two wave washers can be effected by way of a gearbox, for example. The control device can be connected to sensors which are disposed on the orthopedic device such that a response to different requirements is possible while the spring device is in use. The values determined by the sensors are evaluated in the control device, compared with stored programs or criteria and further processed so as to form actuation signals with which the motor is supplied so as to perform an adjustment of the mutual position of the wave washers in one or another direction.

The adjustment device can have a toothing which is coupled to a driven gear wheel or to a driven worm, on account of which very fine setting is possible.

Moreover, such a drive is tested and can be readily adapted to the respective requirements by way of a gearbox.

In a refinement it is provided that all wave washers have the same number of undulations and the same wave shape, so as to enable a harmonic adjustment, on the one hand, and a cost-effective production of wave washers, on the other hand. Apart from a design embodiment of the wave shape as a sinusoidal shape or modifications thereof, a triangular shape, a trapezoidal shape, or a rectangular shape, is also a wave shape according to the present invention.

The spring device is preferably disposed between two mutually repositionable end pieces, wherein the end pieces are repositionable toward one another so as to preload the spring device in an elastic manner, or so as to be able to cause the repositioning counter to a spring force which is applied by the spring device, respectively.

At least one wave washer can be mounted, in particular in a rotationally fixed manner, on or in the end piece, such that only one further wave washer has to be rotated so as to be able to adjust the spring deflection and the spring stiffness. Connector devices or devices for establishing the spring device on other components can be configured or disposed on the end pieces or at least one end piece, such that the spring device can be shipped as a completely assemble component. The end piece, or the end pieces, are capable of being established on the respective component in a rotationally fixed manner in terms of the rotating movement of the wave washer or wave washers. Likewise, an end piece can be configured as a piston which in a hydraulic unit is capable of being impinged with a hydraulic fluid.

At least one wave washer can be mounted in a rotationally fixed manner on the central guide and/or on one of the end pieces. The end pieces are preferably mutually established in a telescopic manner such that a relative movement toward one another in the axial direction is possible. The repositioning direction corresponds substantially to the longitudinal extent of the rotation axis of the wave washers.

The end pieces can preferably be connected to one another by way of the central guide, wherein the central guide simultaneously configures a detent such that the two end pieces cannot be mutually separated. It is possible for the spring preload to be set, or the maximum extent of the spring device to be modified, by way of the length of the central guide. To this end, the central guide is configured so as to be length-adjustable, for example by way of a thread.

A further spring element, in particular a coil spring or a helical spring, for providing a comparatively large spring deflection and a large energy storage capability can be disposed between an end piece and at least one wave washer. As an alternative to a spring element from a helical spring or a coil spring, said spring element can be produced from an elastomer material which is disposed between an end piece and a wave washer at the front side or the end side.

The wave washers preferably have a sinusoidal shape having at least two maxima and two minima, wherein the sinusoidal shape is configured on at least one side which is opposite a spring washer or a spring washer stack. A tilting safeguard is provided on account of a symmetrical design embodiment when exactly two maxima and minima are present. Maximum spring deflections are likewise implementable in this instance.

The invention likewise relates to a hydraulic actuator having a spring device as described above. By way of a combination of a hydraulic actuator and such a spring device it is possible to carry out a variable accumulation of energy and release of energy into a hydraulic system. The hydraulic system is in particular part of an orthopedic device such as an orthotic or a prosthetic. By way of such a design embodiment it is possible to guarantee a coaxial solution of a linear actuator with a spring device in association with easy scalability. The spring device with an adjustable preload is capable of being integrated in the hydraulic actuator, and no additional compensation volume is required on account of the use of a spring device having two wave washers and at least one spring washer disposed therebetween.

BRIEF DESCRIPTION OF THE DRAWINGS

An exemplary embodiment of the invention will be explained in more detail hereunder by means of the appended figures in which.

DETAILED DESCRIPTION

Figure 1:
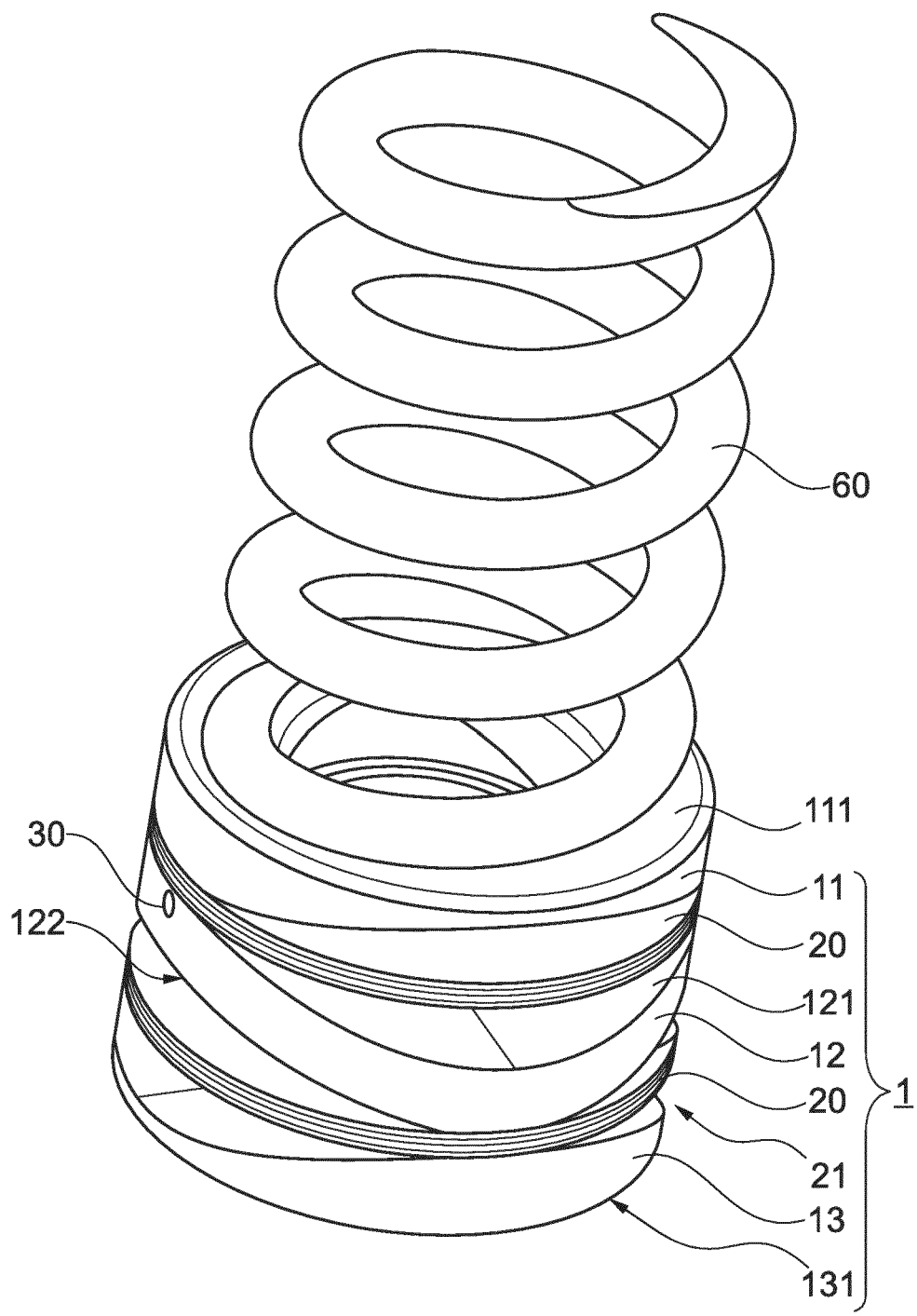
FIG. 1 shows an individual illustration of a spring device having an additional spring element in the rigid position.

FIG. 1 in an individual illustration shows a spring device 1 in combination with a spring element 60 disposed in a row of the disposed spring element 60. The spring device 1 in the exemplary embodiment illustrated is composed of two wave washers 11, 13 at the end sides and one wave washer 12 disposed so as to be centric therebetween. All wave washers 11, 12, 13 are composed of a dimensionally stable material and are embodied so as to be rigid so that no, or no substantial, deformations arise within the wave washers 11, 12, 13 in the event of axial loading. Three spring washers 20 which in the non-loaded state are configured so as to be flat are in each case situated between two wave washers 11, 12; 12, 13. The in each case three spring washers 20 configure a spring washer stack 21. Various numbers of spring washers 20 can be disposed between two wave washers 11, 12, 13 in order for the quantity of energy to be stored or the spring stiffness to be varied. The two wave washers 11, 13 at the end side have a flat rear side 111, 131 which is not provided with a wave contour. A wave-shaped contour which is configured in a sinusoidal manner and has two maxima and two minima is configured on that side of the wave washers 11, 13 that is opposite the flat side 111, 131, wherein the contour is configured so as to be symmetrical. The central wave washer 12 has a wave contour on the upper side 121 as well as on the lower side 122, wherein all wave contours are configured in a mutually corresponding manner such that no, or almost no, intermediate space is present between the wave washers 11, 12, 13 in an alignment of the respective minima and the minima of the neighboring wave washer 11, 12, 13. The wave washers 11, 12, 13 are kept so as to be mutually spaced apart by way of the spring washers 20, or spring washer stacks 21, disposed between the wave washers 11, 12, 13. In the rigid position illustrated, the minima and the maxima of two neighboring wave washers 11, 12, 13, thus wave washers 11, 12, 13 that are disposed behind one another in the axial direction, are in each case assigned so as to be mutually opposite such that no spring deflection is available between the wave washers 11, 12, 13 to the spring washers 20 or the spring washer packs 21. The axial force applied by the wave washers 11, 13 at the end sides is transmitted by way of the bearing points on the central wave washer 12, without a spring washer 20 able to be elastically deformed.

A form-fit element 30 in the form of a clearance into which a pin can be introduced is configured on the radial circumference of the central wave washer 12. In conjunction with an engagement element, it is possible for the central wave washer 12 to be rotated relative to the two other wave washers 11, 13 by way of said form-fit element 30. It is possible on account thereof to set the potential spring deflection which can be exerted by the spring device 1. In the position illustrated, no spring action is possible in relation to the spring washers 20 since the maxima of the upper wave washer 11 are opposite the upper maxima of the central wave washer 12. Likewise, the maxima of the lower wave washer 13 are directly opposite the downwardly directed maxima or minima of the wave washer 12 in the orientation illustrated such that no available spring deflection is situated between the maxima which are in each case mutually opposite. The wave washers 11, 13 at the end sides are preferably mounted in a rotationally fixed manner, either by way of the radially acting locking devices or by way of braking or fixing elements which engage on the flat end sides 131, 111.

Figure 2:
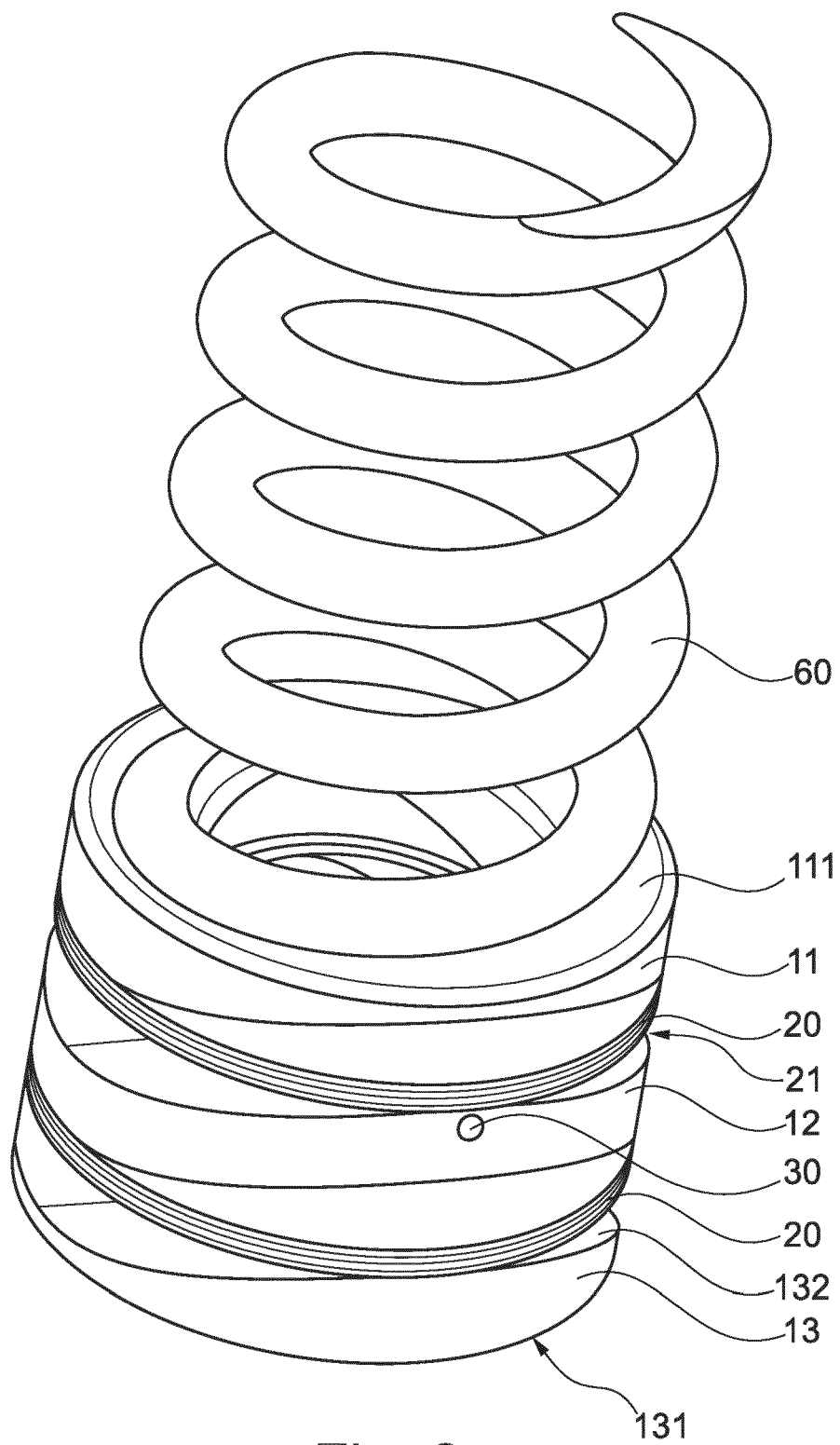
FIG. 2 shows an assembly according to FIG. 1 in the release position.

In the illustration according to FIG. 2, the central wave washer 12 at the identical position of the wave washers 11, 13 at the end sides is rotated by 90° about an axis along the longitudinal extent of the spring device 1, this being highlighted by means of the changed position of the form-fit element 30. On account of said rotation about 90°, the respective wave contours of all spring washers 11, 12, 13 are correspondingly mutually aligned such that the contour profiles of the surfaces which are in each case mutually opposite correspond to one another. The wave washers 11, 12, 13 are held so as to be mutually spaced apart only on account of the spring washers 20, or the spring washer packs 21, respectively, which are disposed therebetween. When an axial force is now applied in the direction toward the end sides 111, 131 of the wave washers 11, 13 at the end sides so as to reposition said wave washers 11, 13 to one another, the spring washers 20 in the spring washer packs 21 are elastically deformed between the respective wave washers 11, 12, 13, while the wave washers 11, 12, 13 remain substantially without deformation. A maximum spring deflection and a maximum quantity of stored energy can be achieved by way of the spring device 1 in such a mutual position of the wave washers 11, 12, 13. The spring element 60 in the form of a coil spring or a helical spring serves as an additional mechanical energy accumulator and is disposed in series with the spring device 1.

Figure 3:
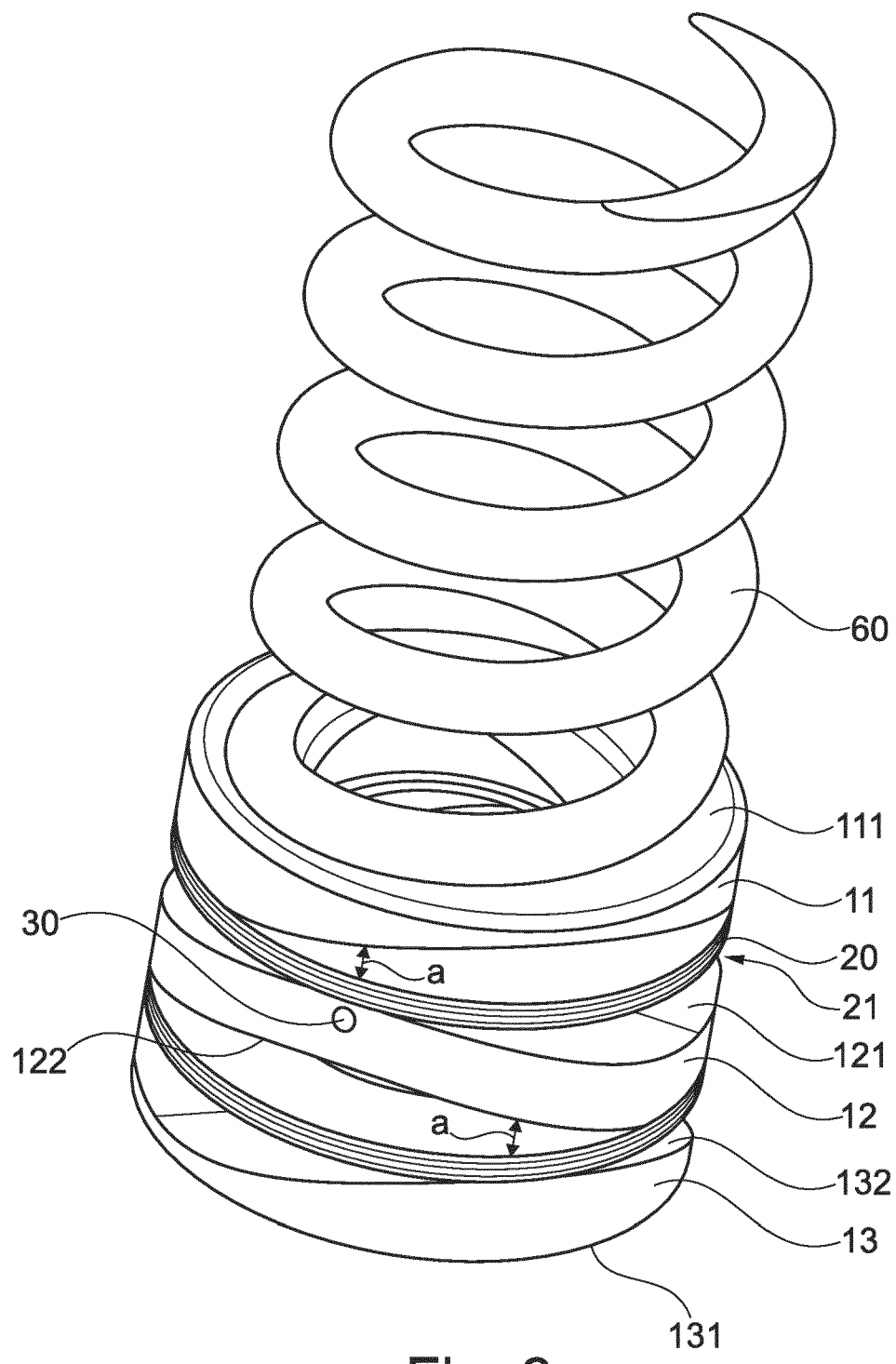
FIG. 3 shows an assembly according to FIG. 1 in an intermediate position.

An intermediate illustration between the two extreme positions according to FIGS. 1 and 2 is illustrated in FIG. 3; the central wave washer 12 is situated approximately in the center between the two extreme positions according to FIGS. 1 and 2. The maximum potential spring deflection is in each case the shortest deflection between two wave washers 11, 12, 13, thus the potential deflection between a bearing location of a spring washer 20, or a spring washer pack 21, and the neighboring wave washer contour in the axial direction. The maximum repositioning deflection, or spring deflection, of the spring device in this instance is composed of the sum of the available spacings a, as shown in FIG. 3.

Figure 4:
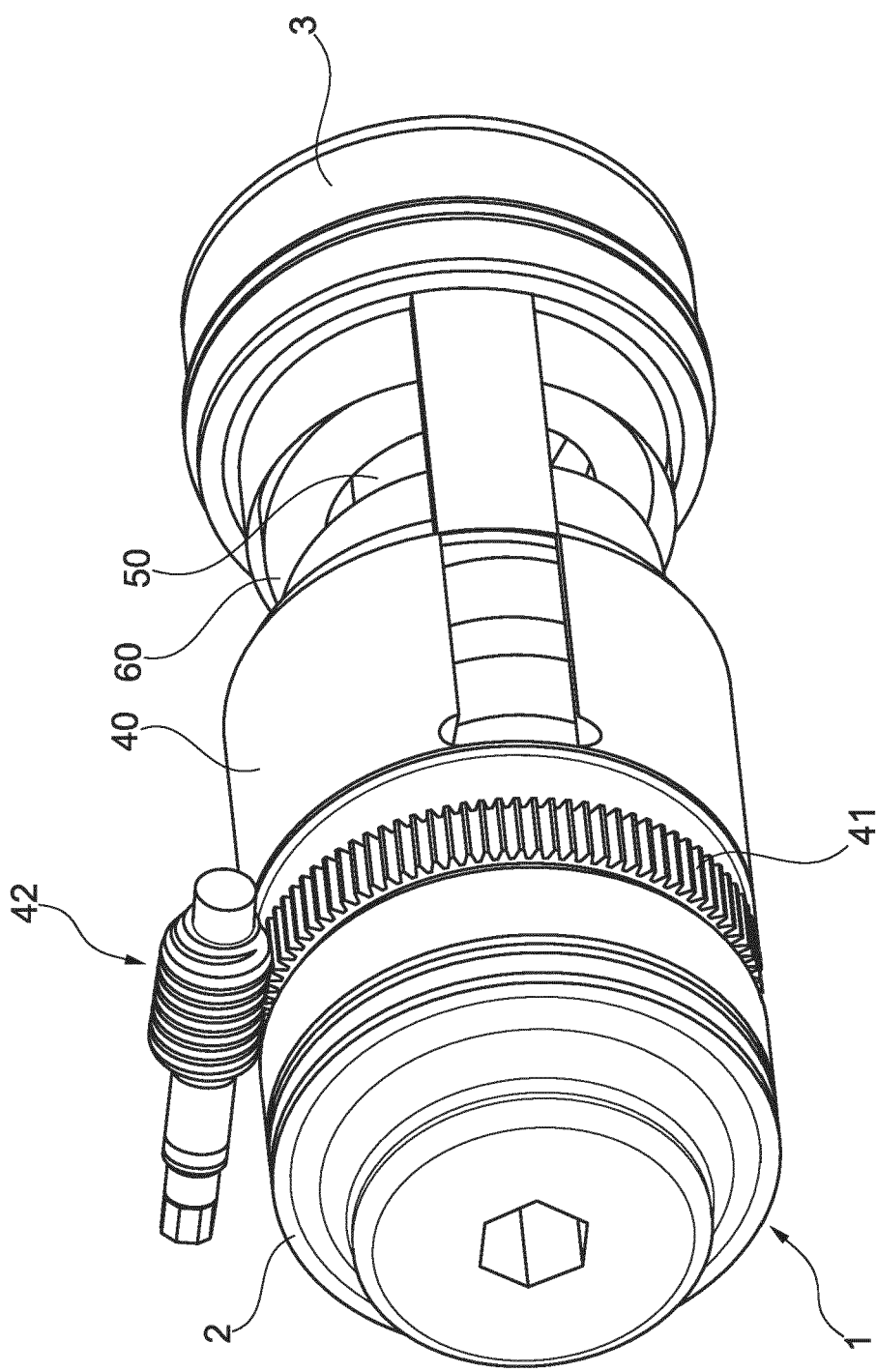
FIG. 4 shows a spring device having an adjustment device in a perspective view.
Figure 5:
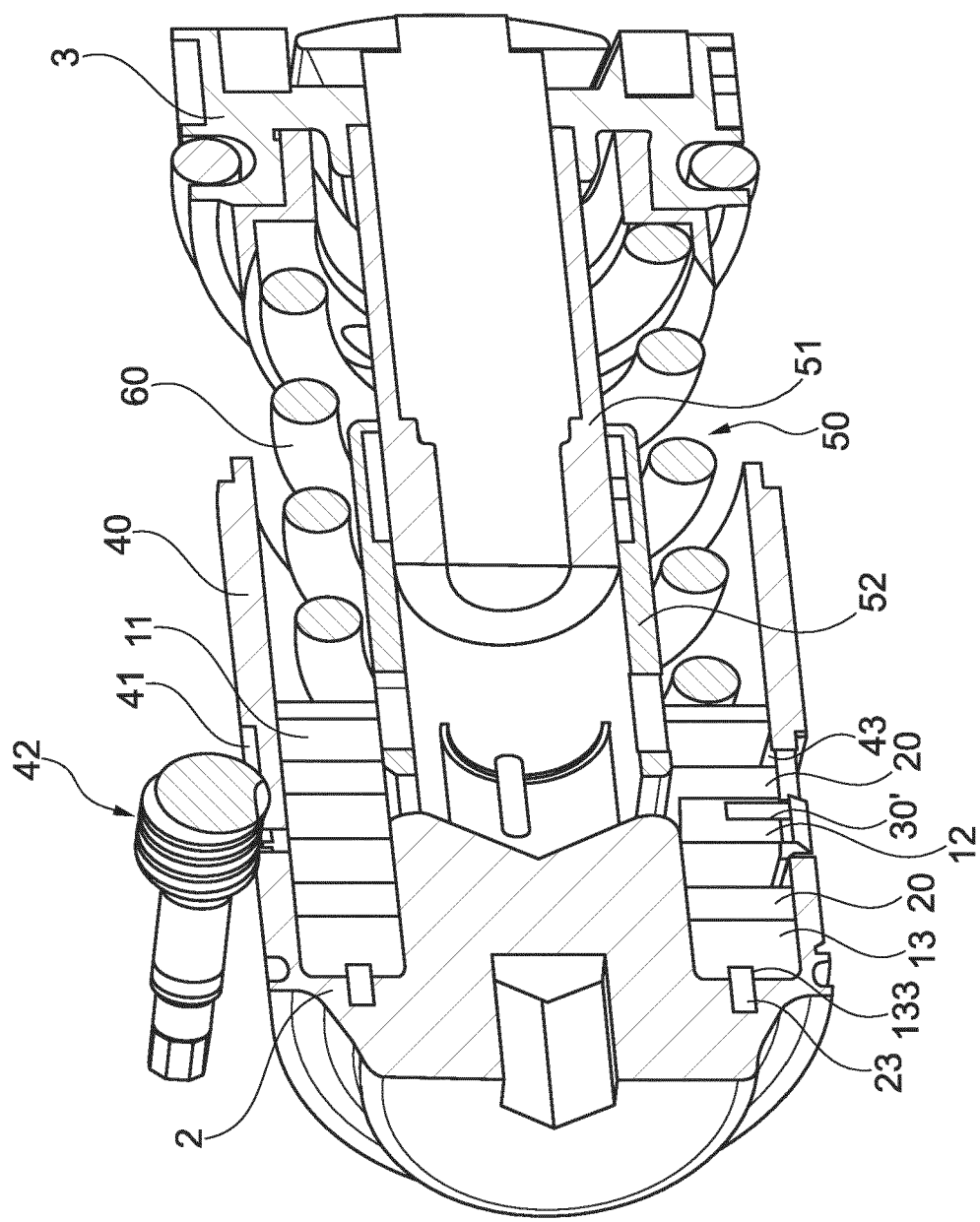
FIG. 5 shows a sectional illustration of FIG. 4.

The spring device 1 is illustrated conjointly with the coil spring or the helical spring 60 in an installed state, so as to be disposed between two end pieces 30, in FIG. 4. The spring installation 1 is situated within an adjustment device 40 which is configured as a sleeve and surrounds the spring washers 20 as well as the wave washers 11, 12, 13. A slot 43 in which a pin or a form-fit element 30' engages, as is shown in FIG. 5, is configured within the sleeve 40. Said pin 30' is introduced into the form-fit element 30 in the central wave washer 12, and by way of rotation of the adjustment device 40 conjointly with the sleeve enables a mutually relative rotation of the spring washers 11, 12, 13. The two end pieces 2, 3 hold the wave washers 11, 12, 13 and the spring washers 20, conjointly with the spring element 60, together. A central guide 50 which penetrates through clearances within the spring washers 20 and the wave washers 11, 12, 13, and about which the coil spring 60 extends is disposed between the end pieces 2, 3. The left end piece 2 on the external side has a thread so as to fasten said left end piece 2 in a hydraulic unit; the opposite end piece 3 is configured as a hydraulic piston and can be repositioned relative to the end piece 2, in the illustrated exemplary embodiment toward the first end piece 2.

A toothing 41 in which a worm 42 driven in a motorized manner engages is configured on the external side of the adjustment device 40. The worm 42 can be driven in two rotating directions by way of a motorized drive which is not illustrated. The adjustment device 40 is rotated in one or another direction about the longitudinal extent of the central guide 50, depending on the driving direction of the worm 42. The pin 30' which is illustrated in FIG. 5, is entrained in a form-fitting manner by the sleeve-type adjustment device 40, and then rotates the central wave washer 12 relative to the two outer wave washers 11, 13 which are held in a rotationally fixed manner.

It can be seen in FIG. 5 that the wave washer 13 that faces the first end piece 2 has two clearances 133 on the flat end side 131, two pins 23 which are established on the end piece 2 protruding into said clearances 133. On account thereof, a rotation of the wave washer 13 at the front sides relative to the central wave washer 12 is enabled, and a rotation relative to the end piece 2 is prevented when the adjustment device 40 is rotated relative to the immovable end piece 2 when the worm 42 is driven.

It can furthermore be seen in FIG. 5 that the central guide 50 is configured in two parts and has two tubular elements 51, 52 which can slide into one another such that the two end pieces 2, 3 are mutually repositionable. The central guide 50 is thus configured so as to be telescopic. It can likewise be seen in FIG. 5 that the pin 30' engages in the radially outward pointing clearance 30 of the central wave washer 12 and is entrained in a form-fitting manner by the slot 43 in the sleeve-type adjustment device 40.

Figure 6:
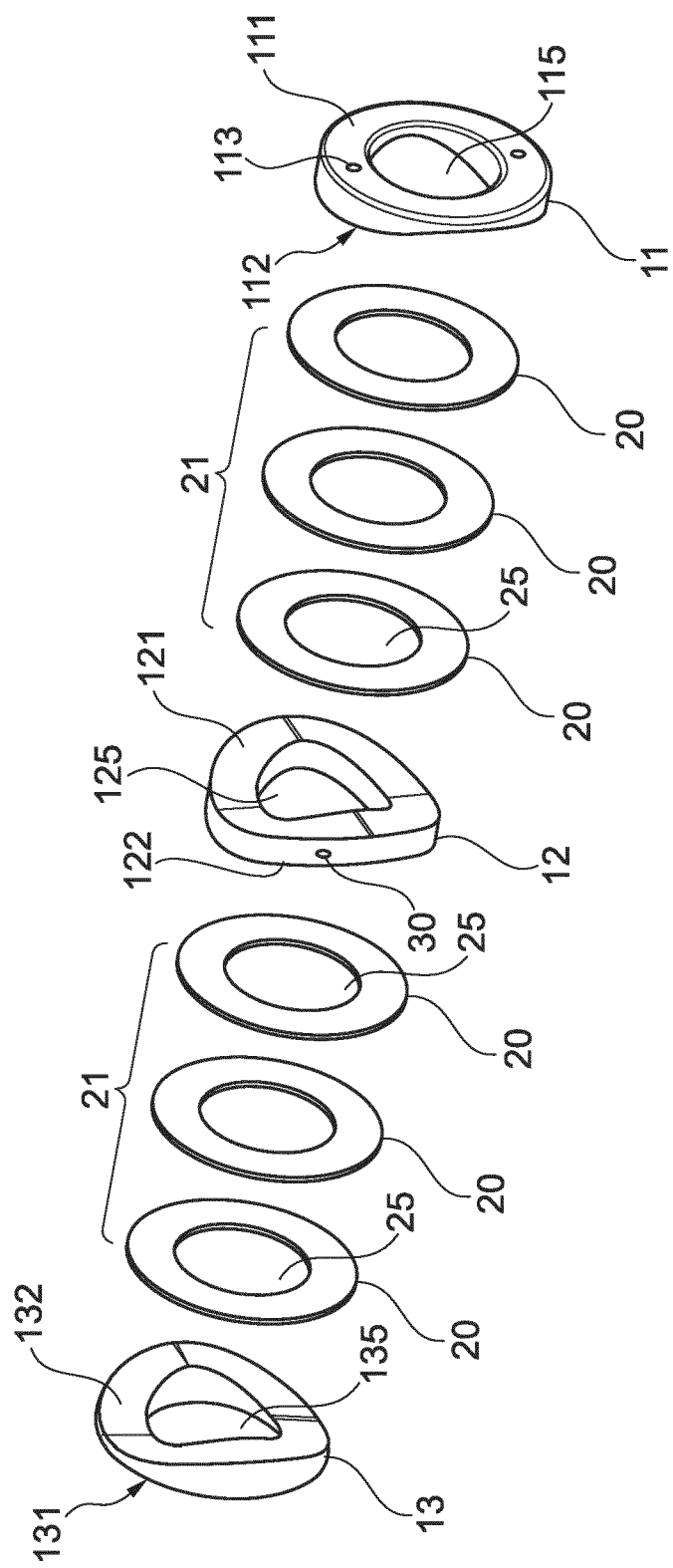
FIG. 6 shows an exploded illustration of a spring device.

The individual parts of a spring device 1 are shown in an exploded illustration in FIG. 6. Three spring washers 20 are in each case combined so as to form one spring washer stack 21 and disposed between two wave washers 11, 12, 13. The wave washers 11, 13 at the end sides, on the flat end sides 111, 131, thereof, have clearances 113 and 133, respectively, in which form-fit elements, for example pins 23, can engage so as to prevent any rotation relative to the end pieces 2, 3. The radially oriented bore 30 which enables the engagement of a form-fit element 30' so as to enable a rotation of the central wave washer 12 relative to the two outer wave washers 11, 13 which are mounted in a rotationally fixed manner is configured only in the central wave washer 12. The respective surface contours on the mutually facing end sides 112, 132 of the wave washers 11, 13 at the end sides correspond to one another; the contour of the central wave washers 12 on the respective surfaces 123, 122 thereof likewise corresponds to the contours of the surfaces 112, 132 facing said surfaces 123, 122. Two maxima and two minima are in each case present on the surface; the central wave washer 12 is configured as a washer undulated on both sides, while the wave washers 11, 13 at the end sides have a wave contour only on an end side 112, 132 and thus can be considered semi-wave washers.

Central clearances 115, 125, 135, 25 which in the exemplary embodiment illustrated are configured so as to be round are configured in the spring washers 20 as well as in the wave washers 11, 12, 13. By way of the round design embodiment of at least the central wave washer 12 on the external circumference as well as in the internal circumference of the clearance 125, it is possible for a rotation to be carried out about the central clearance 50.

Instead of the establishment at the front sides by way of bores 113, 133 on the wave washers 11, 13 at the end sides, a radially oriented establishment, for example on the central clearance 50 may also take place, for example by way of an eccentric design embodiment having a flattening in the tubular element 52, and a corresponding eccentric central clearance 115 of the respective wave washer 11, 13.

Figure 7:
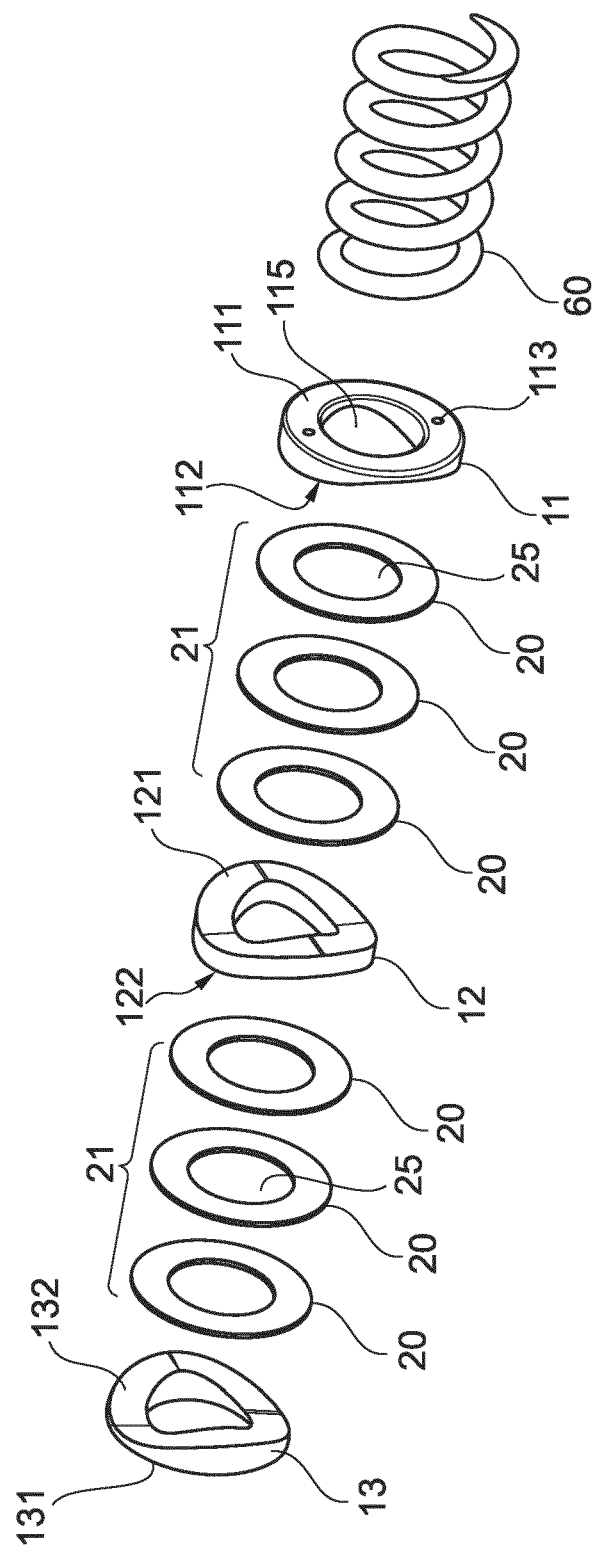
FIG. 7 shows an illustration according to FIG. 6, having a spring element.

The spring device according to FIG. 6, having the spring element 60 which in the form of the coil spring is disposed upstream in the axial direction, is shown in FIG. 7.

Figure 8:
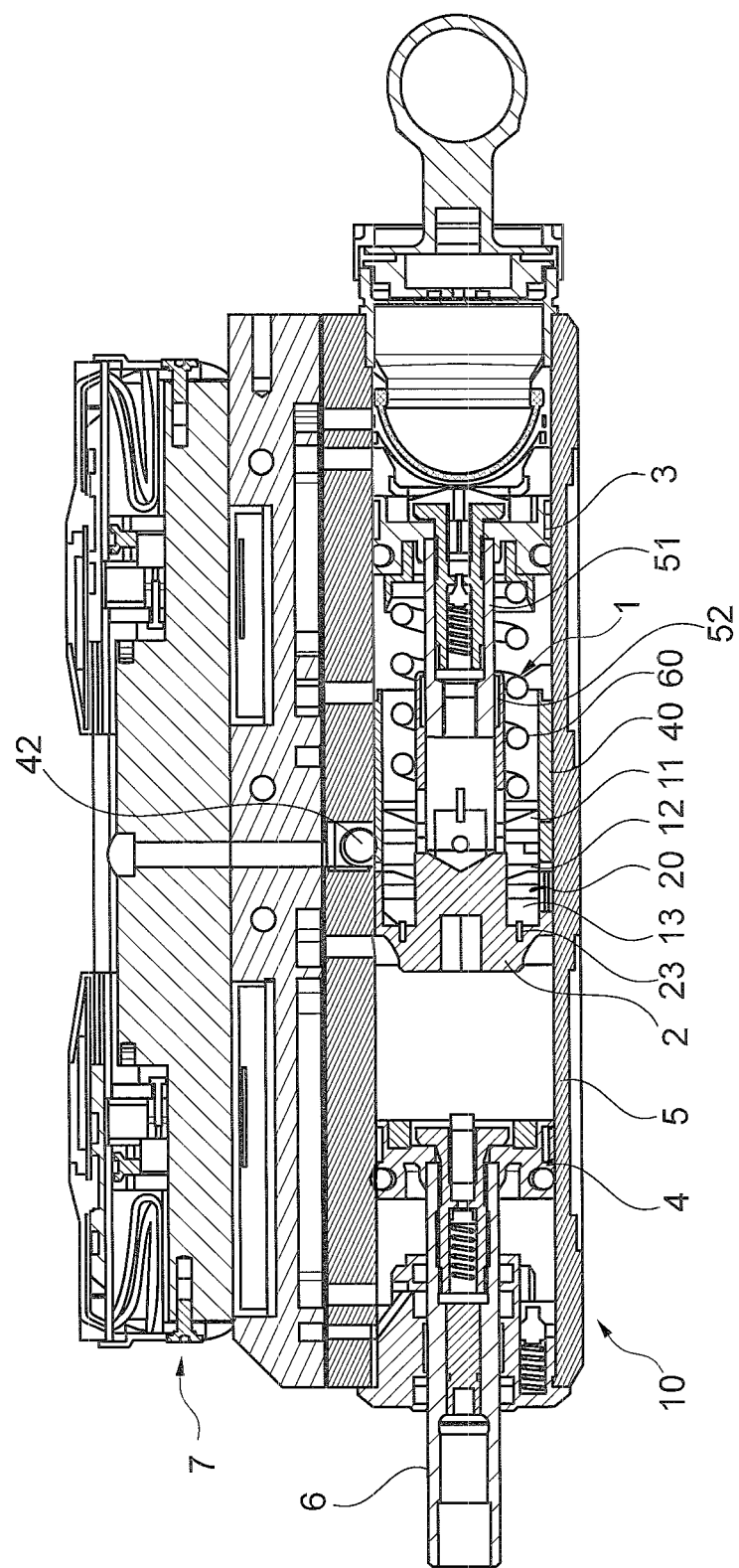
FIG. 8 shows a sectional illustration through a hydraulic actuator having an assembled spring device.

FIG. 8 shows a hydraulic actuator 10 in the form of a hydraulic damper having a housing 5 in which a hydraulic piston 4 is mounted so as to be axially displaceable by way of a piston rod 6. The first end piece 2 is screw-fitted within the housing 5 by way of an external thread; the second end piece 3 of the spring device 1 is configured as a movable piston having a sealing element which is disposed on the external circumference. The hydraulic actuator 10 has an electronic control device 7 by way of which valves can be opened and closed. The drive, not illustrated, for the worm 42 which engages in the external toothing 41 of the adjustment device 40 is likewise activated or deactivated by way of the control device 7. The left wave washer 13 at the end side is mounted so as to be rotationally fixed on the end piece 2 by way of the pins 23. A first spring stack 21, the central wave washer 12, a second spring stack 21, and the second wave washer 11 at the end side adjoin in the axial direction. When the piston rod 6 is repositioned in the direction toward the second end piece 2, hydraulic fluid is pushed by way of hydraulic ducts toward the right, in the direction toward the second end piece 3. The hydraulic pressure compresses the spring element 60 which is supported on the flat lateral face 111, and for example by way of a form-fitting coupling, is mounted in a likewise rotationally fixed manner in the sleeve-type adjustment device 40 by way of the helical spring 60. An axial force which acts in the direction toward the second wave washer 13 at the end side is exerted by the spring element 60. At a mutual position of the wave washers 11, 12, 13 according to FIG. 1, the spring washers 20 would not have any spring deflection available between the wave washers 11, 12, 13 such that the coil spring 60 would be the only energy accumulator device. When another quantity of stored energy is required, the drive, not illustrated, is activated, the worm 42 engages in the toothing 41, rotates the adjustment device 40 by 90° for example, until the position according to FIG. 2 is reached. An additional spring deflection and an additional spring force, or quantity of stored energy, respectively, is then made available.

Any position can be assumed between the two extreme positions according to FIGS. 1 and 2, such that each spring deflection between zero and the maximum spring deflection can be set.

Figure 9:
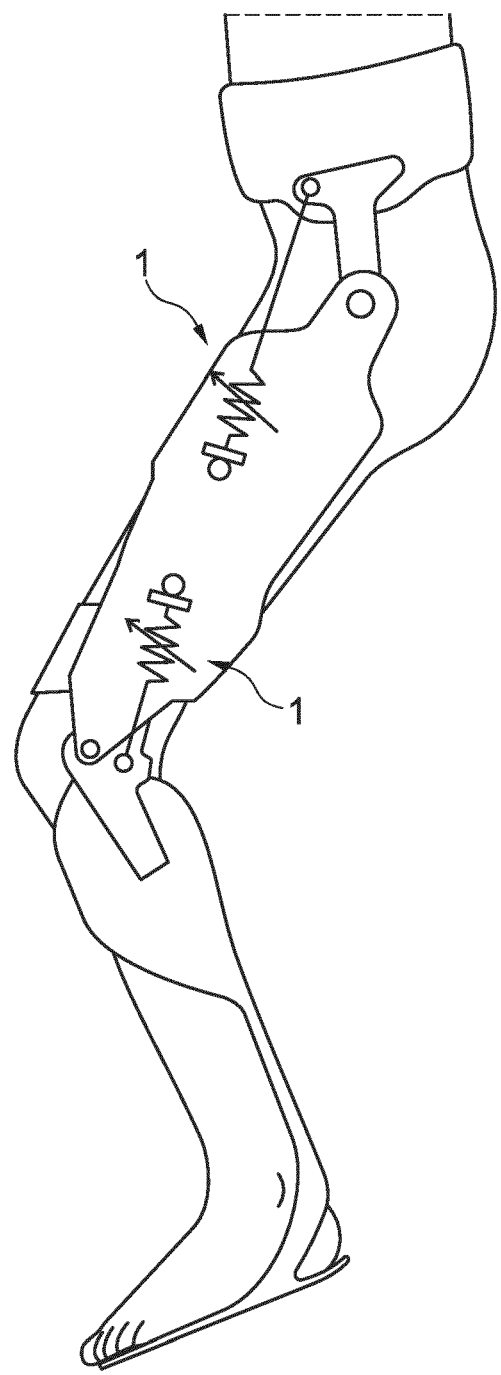
FIG. 9 shows exemplary applications of the spring device in an orthotic.

Potential arrangements of the spring device 1 or else of the hydraulic actuator according to FIG. 8 are shown in FIG. 9 in which the schematically indicated spring devices 1 are disposed on the external side of an orthotic. The adjustable spring device 1 is configured between a hip belt or a hip shell and an upper-leg frame, as well as between an upper-leg frame and a lower-leg part of a three-part orthotic. The orthotic illustrated has a lower-leg part with a foot part, wherein the foot part is not connected in an articulated manner to the lower-leg part. In principle, it is also possible for a spring device 1 to be disposed between a foot plate and a lower-leg part, as long as said plate and said lower-leg part are connected to one another in an articulated manner.

Figure 10:
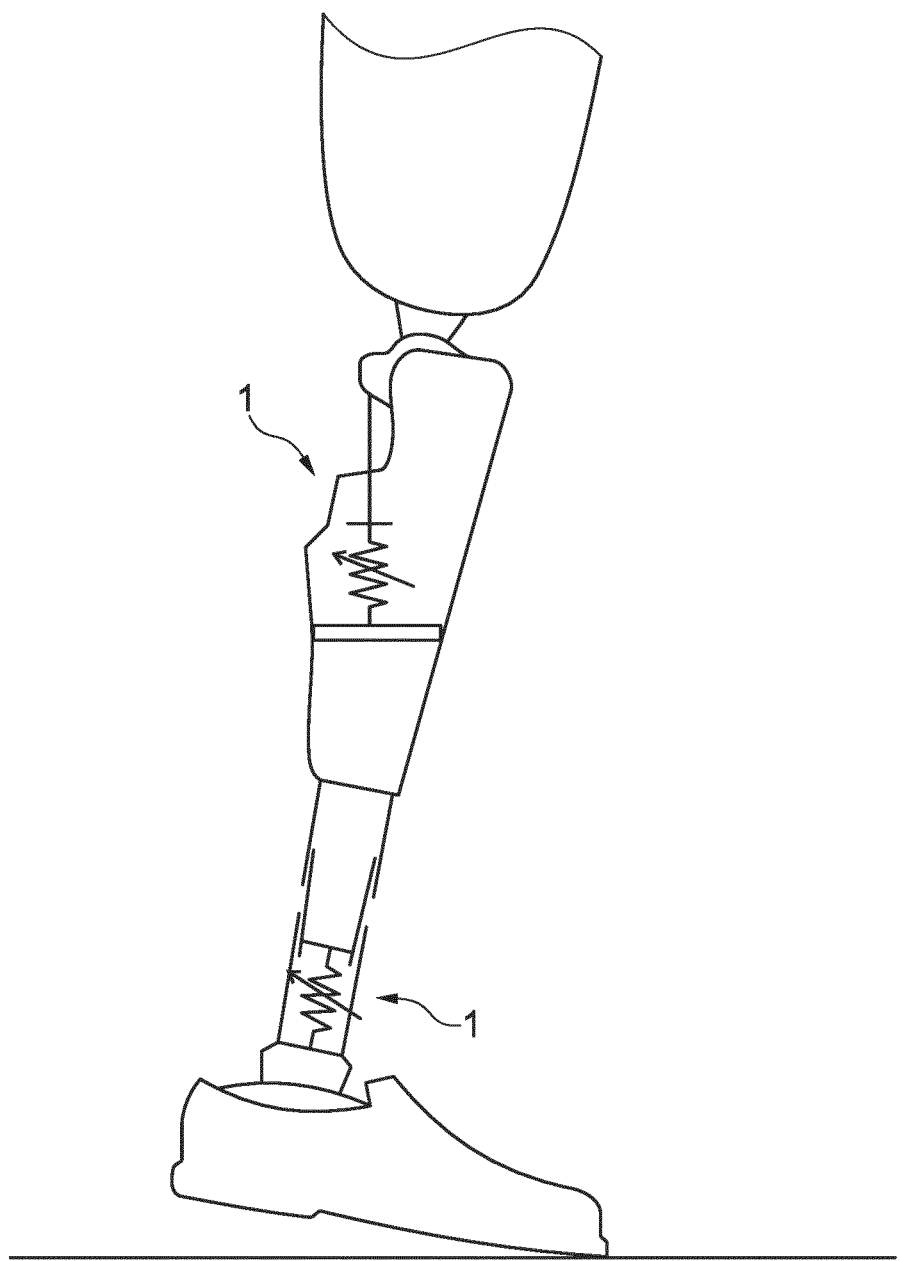
FIG. 10 shows exemplary applications of the spring device in a prosthetic.

One variant of the invention provides the disposal of the spring device 1 in a prosthetic, as is illustrated in FIG. 10. Two spring devices 1 or hydraulic actuators can be disposed between a prosthetic foot and a lower-leg part, or in a prosthetic knee joint between a lower-leg part and an upper-leg part. The spring device 1 between the prosthetic foot and the lower-leg tube permits an adjustable accumulation of energy in association with an axial loading along the lower-leg tube in the direction toward the prosthetic knee joint. The spring device 1 disposed between the lower-leg part and the prosthetic knee joint serves, for example, for storing energy from movements during flexion and for releasing said energy during extension.

Figure 11:
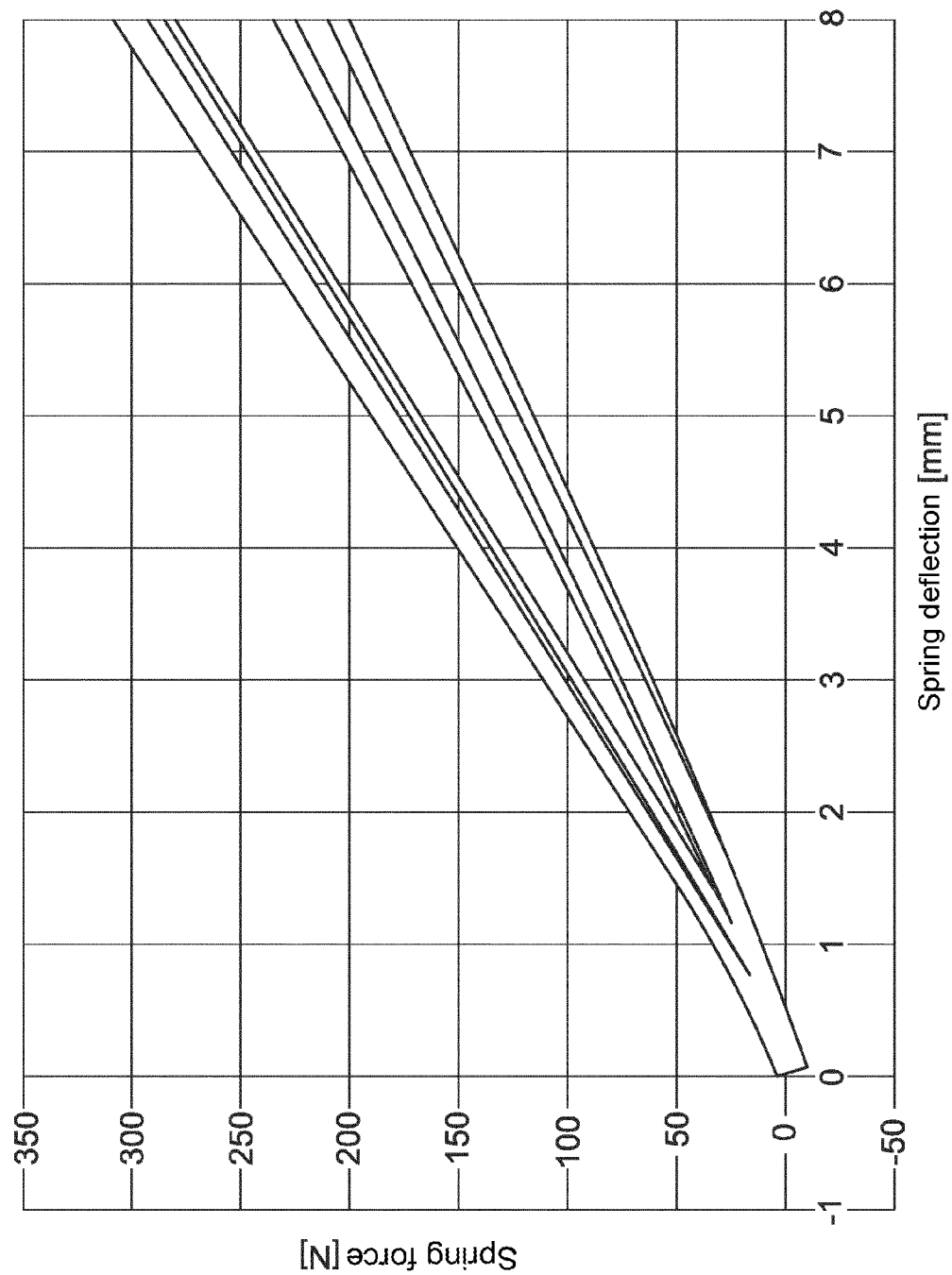
FIG. 11 shows an illustration of spring deflection over spring force.

A diagram of spring deflection A over spring force N is shown in FIG. 11, wherein it can be seen that the spring force to be received as well as the maximum spring deflection can be adjusted by the mutual adjustment of the wave washers 11, 12, 13.

The stiffness of the spring device 1 can be varied without the length of the spring device 1 being changed. The quantity of energy to be stored and thus also to be released can likewise be varied in a stepless manner. Apart from the motorized adjustment by way of the worm 42, manual adjustment can also take place by way of a lever or any other access to the adjustable wave washer. Variations in terms of the maximum spring deflection and of the quantity of energy to be stored can be readily performed by disposing in series a plurality of wave washers with a wave contour on both sides and spring washers disposed therebetween. The rotatably mounted wave washers are individually adjustable so as to be able to set any combination of activated, partially activated and deactivated spring washers 20 or spring stacks 21.

I claim:
1. A spring device comprising:
   at least two wave washers;

at least one spring washer disposed between the wave washers;

wherein the wave washers are mounted so as to be capable of being rotated relative to one another, and wherein the at least one spring washer is flat in a non-loaded state and situated between two rigid wave washers.

2. The spring device as claimed in claim 1, wherein the at least one spring washer includes a plurality of spring washers as a spring washer stack that is disposed between the wave washers.

3. The spring device as claimed in claim 1, wherein the at least two wave washers are disposed on an end of that side that faces away from the at least one spring washer so as to be flat.

4. The spring device as claimed in claim 1, wherein the at least two wave washers are configured so as to be undulated on both sides that face the at least one spring washer and is disposed between two spring washers.

5. The spring device as claimed in claim 1, wherein the at least two wave washers and the at least one spring washer have in each case a central clearance and are mounted on a central guide.

6. The spring device as claimed in claim 1, wherein at least one of the wave washers is coupled to an adjustment device by way of a form-fit element.

7. The spring device as claimed in claim 6, wherein the form-fit element is configured as a clearance, a protrusion, a pin, a shoulder, an eccentric, or a toothing.

8. The spring device as claimed in claim 6, wherein the adjustment device at least partially surrounds the at least one of the wave washers or is disposed within the at least one of the wave washers.

9. The spring device as claimed in claim 6, wherein the adjustment device is driven in a motorized manner.

10. The spring device as claimed in claim 9, wherein the adjustment device has a toothing which is coupled to a driven gear wheel or a driven worm.

11. The spring device as claimed in claim 1, wherein all wave washers have the same number of undulations and the same wave shape.

12. The spring device as claimed in claim 1, wherein the spring device is disposed between two mutually displaceable end pieces.

13. The spring device as claimed in claim 12, wherein the at least two wave washers are mounted in a rotationally fixed manner on at least one of a central guide and one of the end pieces.

14. The spring device as claimed in claim 12, wherein the end pieces are mutually established in a telescopic manner.

15. The spring device as claimed in claim 12, wherein the end pieces are connected to one another by way of a central guide.

16. The spring device as claimed in claim 12, wherein the spring element is disposed between one of the end pieces and at least one of the wave washers.

17. The spring device as claimed in claim 1, wherein the at least two wave washers have a sinusoidal, triangular, trapezoidal, or rectangular shape having at least two maxima and two minima.

18. A hydraulic actuator comprising the spring device of claim 1.

19. A spring device comprising:
a plurality of wave washers;
at least one spring washer disposed between the wave washers;
wherein the wave washers are rotatably mounted relative to one another, and wherein the spring washer is flat in a non-loaded state and situated between two rigid wave washers of the plurality of wave washers.

20. The spring device as claimed in claim 19, wherein the at least one spring washer includes a plurality of spring washers as a spring washer stack, the spring stack being disposed between the wave washers.

* * * * *